US009278355B2

(12) United States Patent
Kajiyama et al.

(10) Patent No.: US 9,278,355 B2
(45) Date of Patent: Mar. 8, 2016

(54) NUCLEIC ACID AMPLIFICATION DEVICE

(75) Inventors: Tomoharu Kajiyama, Higashiyamato (JP); Masataka Shirai, Higashimurayama (JP); Hideki Kambara, Hachioji (JP)

(73) Assignee: Hitachi, Ltd., Tokyo (JP)

( * ) Notice: Subject to any disclaimer, the term of this patent is extended or adjusted under 35 U.S.C. 154(b) by 1005 days.

(21) Appl. No.: 12/292,167

(22) Filed: Nov. 13, 2008

(65) Prior Publication Data

US 2009/0215162 A1 Aug. 27, 2009

(30) Foreign Application Priority Data

Feb. 21, 2008 (JP) ................................ 2008-040248

(51) Int. Cl.

*C12N 15/10* (2006.01)
*C12Q 1/68* (2006.01)
*B01L 3/00* (2006.01)

(52) U.S. Cl.

CPC ........... *B01L 3/50851* (2013.01); *B01L 3/5025* (2013.01); *B01L 3/50857* (2013.01); *B01L 2200/0668* (2013.01); *B01L 2300/0819* (2013.01)

(58) Field of Classification Search

CPC .............. B01L 3/50851; B01L 3/5025; B01L 2300/0819; B01L 2200/0668; B01L 3/50857
See application file for complete search history.

(56) References Cited

U.S. PATENT DOCUMENTS

| | | | | |
|---|---|---|---|---|
| 6,391,559 | B1 * | 5/2002 | Brown et al. | 435/6.11 |
| 6,713,298 | B2 * | 3/2004 | McDevitt et al. | 435/287.8 |
| 2002/0045272 | A1 | 4/2002 | McDevitt et al. | |
| 2008/0102469 | A1 | 5/2008 | Kajiyama et al. | |

FOREIGN PATENT DOCUMENTS

JP 2007-319028 5/2006

OTHER PUBLICATIONS

Liu, Yingjie, et al., "Microfabricated Polycarbonate CE Devices for DNA Analysis", Analytical Chemistry, vol. 73, No. 17, Sep. 1, 2001, pp. 4196-4201.
Margulies, Marcel, et al., "Genome Sequencing in Microfabricated High-density Picolitre Reactors" Nature, Articles, vol. 437, Sep. 15, 2005, pp. 376-380; Errata & Corrigenda, Nature, vol. 441, May 4, 2006, p. 120.

(Continued)

*Primary Examiner* — Gautam Prakash
(74) *Attorney, Agent, or Firm* — Mattingly & Malur, PC

(57) ABSTRACT

This invention provides a nucleic acid amplification device whereby the abundance of a target molecule can be maintained before and after a step of separately amplifying a sample such that highly accurate analysis results that can be applied to gene expression analysis can be obtained. Also, a nucleic acid amplification device having a structure in which a plurality of minute reaction cells each comprising a set of a bead-retaining space capable of retaining a single analysis bead and a reagent reaction space retaining no bead but having a volume that is large enough to cause a reagent reaction therein are positioned so as to form a planar face is provided.

2 Claims, 21 Drawing Sheets

(56) References Cited

OTHER PUBLICATIONS

Dressman, Devin, et al., "Transforming Single DNA Molecules into Fluorescent Magnetic Particles for Detection and Enumeration of Genetic Variations", PNAS, vol. 100, No. 15, Jul. 22, 2003, pp. 8817-8822.

Barski, Artem, et al., "High-Resolution Profiling of Histone Methylations in the Human Genome", Cell 129, May 18, 2007, © 2007, Elsevier Inc., pp. 823-837.

* cited by examiner (1) Cylindrical shape (2) Hexagonal shape

NUCLEIC ACID AMPLIFICATION DEVICE

CLAIM OF PRIORITY

The present application claims priority from Japanese patent application JP 2008-040248 filed on Feb. 21, 2008, the content of which is hereby incorporated by reference into this application.

BACKGROUND OF THE INVENTION

1. Field of the Invention

The present invention relates to a gene analysis technique. More specifically, the present invention relates to a nucleic acid amplification device in which target molecules to be analyzed, such as mRNA, are separately amplified on the surfaces of solid phases such as beads in a manner such that the utilization of the target molecules is improved and mixing or excessive amplification of the target molecules can be resolved.

2. Background Art

For a gene sequence analysis technique, amplification of a target molecule to be analyzed, such as mRNA or a DNA fragment in a state in which the sequence information is preserved therein, is an important technique. One example thereof is a sequence analysis system using pyrosequencing (NATURE, Vol. 437, pp. 376-380 (2005)). In such system, it is necessary for target molecules to be separately amplified such that one type of a target molecule to be analyzed is immobilized on the surface of a single bead.

Meanwhile, as an elemental technique for amplification in a separate manner, there exists a method involving separation with the use of aqueous micelles in oil (PNAS, Vol. 100, No. 15, pp. 8817-8822 (2003)). In this method, stirring of two phases (an aqueous phase and an oil phase) is performed to form aqueous micelles each retaining a set of a bead, a target molecule, a reagent necessary for amplification of nucleic acid, and the like, and then nucleic acid amplification is carried out on the bead surface with a thermal cycle. Ideally, a single micelle should contain a single bead and a single target molecule. However, it is impossible to achieve such conditions for every micelle. Thus, a micelle containing a bead but no target molecule or a micelle containing a target molecule but no bead could exist. Furthermore, a micelle containing a plurality of beads and/or target molecules or a micelle containing neither bead nor target molecule could exist (PNAS, Vol. 100, No. 15, pp. 8817-8822 (2003)). In a case in which a single micelle contains a plurality of target molecules, a mixture of target molecules is generated upon amplification, making sequence analysis impossible. In addition, in a case in which a micelle contains a target molecule but no bead, the target molecule cannot be amplified on the bead surface, resulting in loss of the target molecule. Further, in a case in which a micelle contains a plurality of beads, amplification derived from an identical target molecule is carried out on the surfaces of a plurality of beads, resulting in excessive analysis, which is problematic.

Furthermore, an amplification method wherein an assembly region (colony) is generated on a part of the flat plate surface of a glass slide or the like has been reported (Cell, Vol. 129, pp. 823-837 (2007)). According to this method, a flat plate having amplification primers immobilized thereon is used to cause complementary strand binding between the primers on the flat plate and target molecules, provide that the concentration distribution of the molecules is determined in a manner such that a certain distance is secured between the target molecules. Then, primer elongation and complementary strand binding (bridge type) are repeatedly induced with the use of primers surrounding each target molecule, such that amplified product colonies are formed. The method is problematic in that excessive amounts of target molecules are necessary due to low efficiency of complementary strand binding of primers to a plane face, and in that complementary strand binding of a plurality of neighboring target molecules might cause binding of amplified product colonies, resulting in mixing of amplified products.

SUMMARY OF THE INVENTION

As described above, in the cases of the conventional techniques, the following points are problematic for amplification of a target molecule: (1): a droplet (micelle) does not contain a bead and thus a target molecule contained in such micelle cannot be analyzed; (2): a micelle contains a plurality of beads and thus a plurality of beads each having an amplification product (derived from a target molecule) immobilized thereon are generated, resulting in excessive analysis. Therefore, before and after the amplification step in preanalysis treatment, the abundance of a target molecule cannot be maintained and the abundance of the target molecule used cannot be ensured, even with statistical analysis of the frequency of the acquisition of the corresponding sequence information. Thus, it has been difficult to apply the conventional techniques to gene expression analysis.

Further, the size of each micelle, i.e., the volume thereof, depends on the extent of stirring upon micelle formation, and such size significantly varies. Hence, the amount of a reagent for an amplification reaction varies and thus the amounts of the resulting amplified products on a bead also significantly vary. Therefore, for instance, in the case of analysis using the aforementioned pyrosequencing method, the signal intensity derived from each individual bead significantly varies, resulting in an insufficient dynamic range of a detection system. This causes incidents involving failures of analysis due to generation of signals below the detection limit or signals exceeding the detection sensitivity, which have been problematic.

It is an objective of the present invention to provide a highly efficient and highly accurate nucleic acid amplification device by solving the problems of the above conventional techniques.

In order to achieve the above objective, the present inventors devised a massively parallel amplification device whereby microbeads having diameters of several tens of micrometers or less can be separately reacted.

Specifically, the present invention relates to an example of a nucleic acid amplification device in which a plurality of reaction cells each comprising a set of a $1^{st}$ space capable of retaining a single $1^{st}$ bead and a $2^{nd}$ space facing the $1^{st}$ space are positioned so as to form a planar face, provided that the $1^{st}$ space and the $2^{nd}$ space are positioned in a manner such that the $1^{st}$ bead is not located in a region in which the $1^{st}$ space and the $2^{nd}$ space do not overlap each other as viewed from the planar face.

In one embodiment, a bead-retaining space ($1^{st}$ space capable of retaining a single $1^{st}$ bead) and a reagent reaction space ($2^{nd}$ space facing the $1^{st}$ space) are directly and vertically connected to each other. In such case, a single reaction cell (minute reaction cell) is constructed to retain a single bead, provided that the following conditions for the relationship between the diameter "r" of the bead and the height or diameter of each space are satisfied:

1) the height of the bead-retaining space is larger than "r/2" and smaller than "3r/2;"

2) the sum of the height of the bead-retaining space and the height of a reagent-retaining space is "2r" or less; and 3) the diameter of the bead-retaining space is larger than "r" and smaller than "2r."

The bead-retaining space and the reagent reaction space may be connected to each other with a capillary having a diameter smaller than that of a bead.

Also, according to the present invention, a nucleic acid amplification device having a structure is provided, in which a plurality of minute reaction cells each comprising a set of a bead-retaining space 1 capable of retaining a single analysis bead, a reagent reaction space in which no bead is retained, and a bead-retaining space 2 capable of retaining a single bead that differs from the analysis bead are positioned so as to form a planar face. In such device, for example, a bead having a sample nucleic acid immobilized thereon can be retained in a bead-retaining space 2.

In one embodiment, a reagent reaction space is located between a bead-retaining space 1 and a bead-retaining space 2. In such case, a single minute reaction cell is constructed to retain a single bead, provided that the following condition for the relationship between the diameter "r" of the bead and the height or diameter of each space are satisfied:

1) the heights of the bead-retaining spaces 1 and 2 are each larger than "r/2" and smaller than "3r/2;"

2) the sum of the height of the bead-retaining space 1 or 2 and the height of the reagent-retaining space is "2r" or less; and 3) the diameters of the bead-retaining spaces 1 and 2 are each larger than "r" and smaller than "2r."

In another embodiment, the bead-retaining space 1 and the bead-retaining space 2 are connected to each other with a capillary having a diameter smaller than that of a bead.

In the case of the device of the present invention, flow cell formation can be achieved by assembling the minute reaction cells. In addition, formation of separate minute reaction cells can be realized by installing a member (top plate) that covers the openings of the cells. Preferably, such member (top plate) that covers the openings of the cells has a layer made of an elastic material such as a sealing material.

In addition, a space (in each minute reaction cell) connected to a flow cell does not necessarily have a vertical wall surface. When the wall surface is inclined outward as viewed from the flow cell, an excess bead can readily exit such space.

EFFECTS OF THE INVENTION

According to the present invention, when a massively parallel nucleic acid sequence technique is applied to gene expression analysis, samples that cannot be analyzed are reduced, and thus analysis accuracy can be improved. In addition, analysis efficiency can be improved by reducing samples that cannot be analyzed upon conducting massively parallel analysis.

DESCRIPTION OF THE PREFERRED EMBODIMENTS

The present invention is hereafter described in greater detail with reference to the following examples, although the technical scope of the present invention is not limited thereto.

EXAMPLE 1

The Basic Structure of the Device

Figure 1:
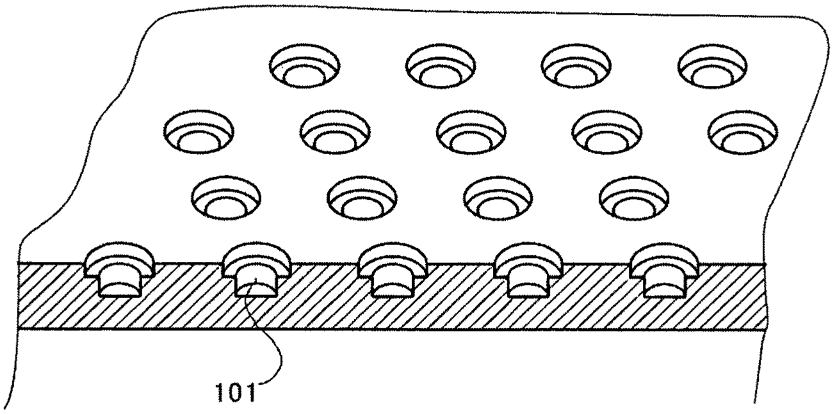
FIG. 1 shows a cross-sectional view of a part of the device.
Figure 2:
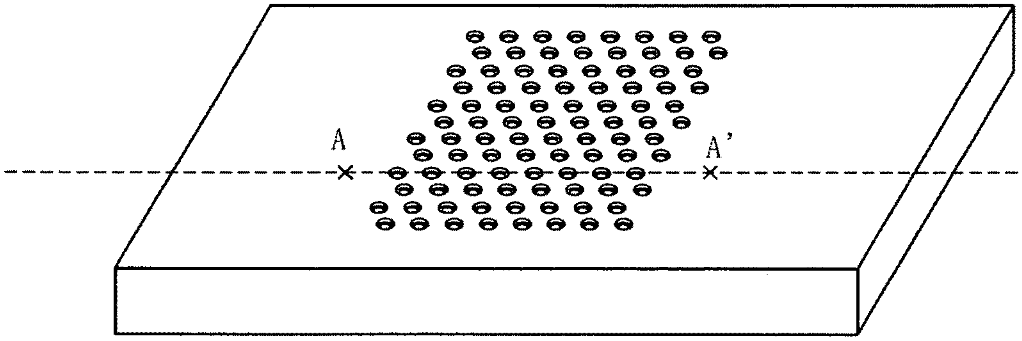
FIG. 2 shows an overall view of the device.

Example 1 shows the basic structure of the device of the present invention. FIG. 1 shows a cross-sectional view of one part of the device for subjecting nucleic acid as a target molecule to parallel amplification of the present invention. FIG. 2 shows an overall view of the device. The cross-sectional view at the dashed line A-A' in FIG. 2 corresponds to FIG. 1. Herein, a structure in which a plurality of minute reaction cells 101 are formed on the surface of a rectangular flat plate is shown. However, the device of the present invention is not limited thereto.

Figure 3:
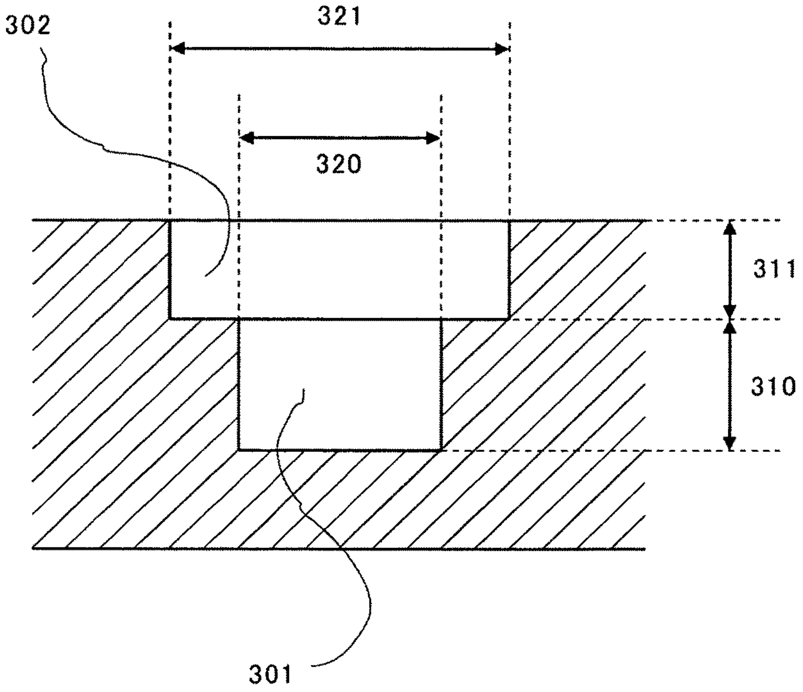
FIG. 3 shows an enlarged view of a minute reaction cell.

FIG. 3 shows a cross section of a minute reaction cell. In this Example, a minute reaction cell has a columnar bead-retaining space 301 and a columnar reagent reaction space 302. The heights of the spaces are denoted by reference numerals 310 and 311, and the diameters thereof are denoted by reference numerals 320 and 321, respectively. In addition, the cell shape is not limited to such a columnar shape as long as effects of the present invention described below can be obtained.

The height 310 and the diameter 320 are determined to satisfy the following conditions. Given that the diameter of a bead to be used is "r," the height 310 is determined to satisfy the condition of "r/2"<height 310<"3r/2." The sum of the height 310 and the height 311 is determined to be "2r" or less. In addition, regarding the diameter, it is necessary for the diameter 320 of the bead-retaining space to satisfy the condition of "r"<diameter 320<"2r." Under the above conditions, a reaction cell can retain a single bead.

Flow Cell Formation in the Device

Figure 4:
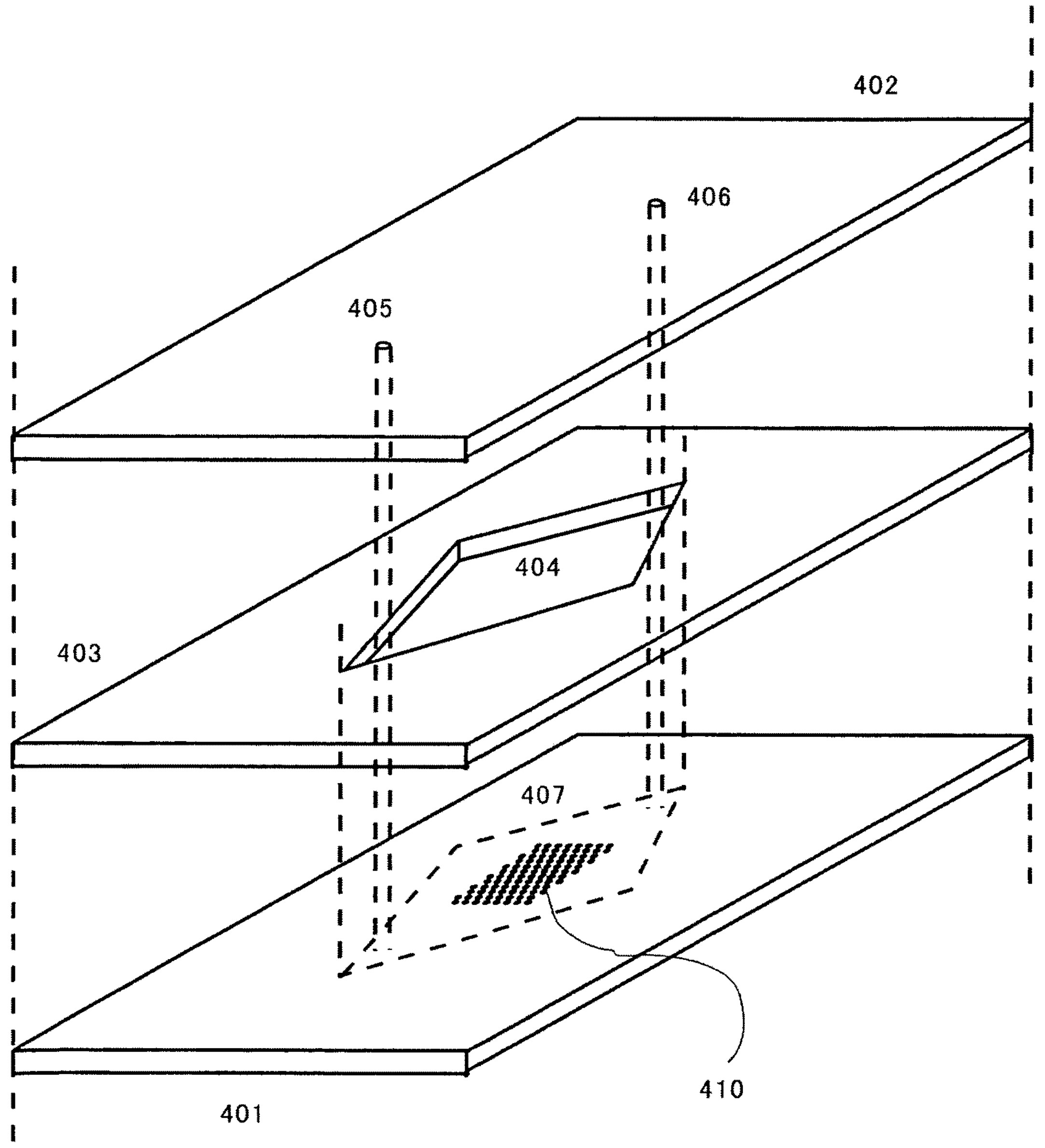
FIG. 4 shows an assembly drawing of flow cell formation in the device.

FIG. 4 shows flow cell formation in the device. As shown in FIG. 4, the device has a structure in which a parallel amplification device 401, a top plate 402, and a spacer material 403 are layered. The spacer material 403 has a space 404 serving as a flow cell in the center portion. The space 404 is projected so as to correspond to an area 407 on the device 401. A reference numeral 410 denotes a group of minute reaction cells on the device 401. The top plate 402 has an inlet 405 and an outlet 406 such that, when a solution containing beads is introduced via the inlet 405, the beads are retained in minute reaction cells arranged in the flow cell.

Figure 5:
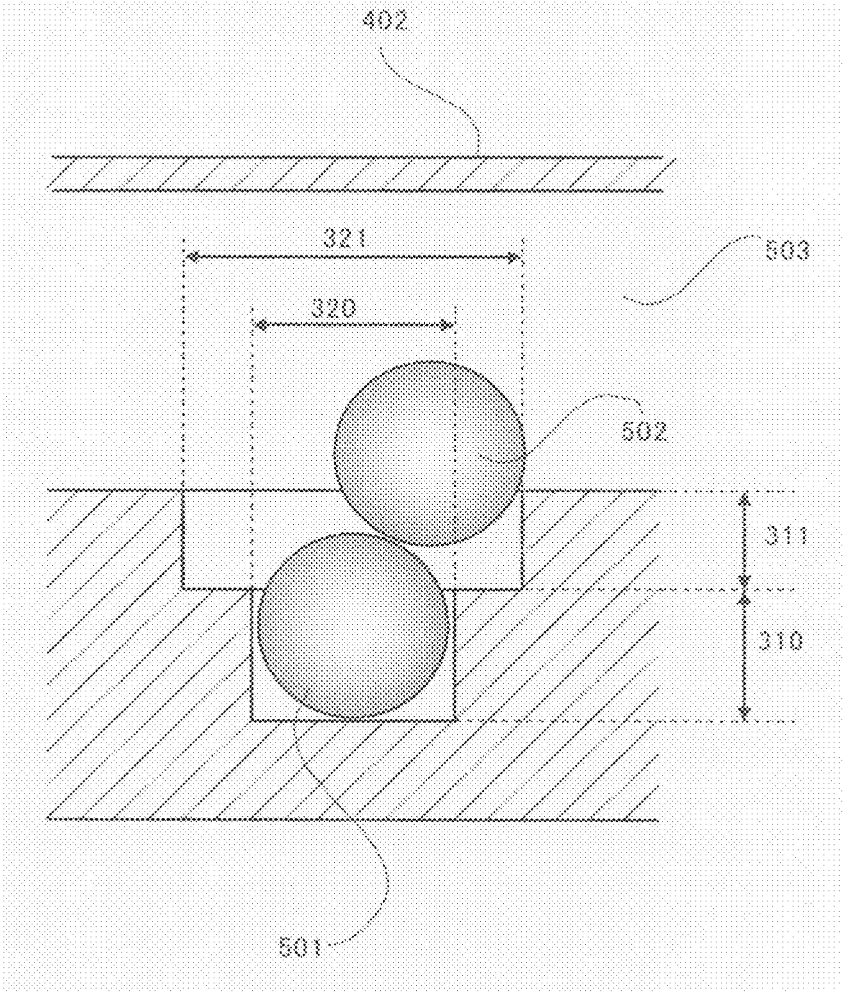
FIG. 5 shows an explanatory view of the mechanism in which a bead is retained in a bead-retaining space.

FIG. 5 shows a mechanism by which a bead is retained in a bead-retaining space. FIG. 5 shows a bead 501 and a bead 502. A space 503 is filled with a solution containing beads. Given that the left side of the figure is the inlet side and the right side is the outlet side, a solution is repeatedly introduced from the left side to the right side and a bead is partially stuck in a minute reaction cell as shown in the figure. The bead 501 is entirely inside the bead-retaining space of a minute reaction cell and thus the left-to-right flow of the solution cannot readily cause the bead to exit the cell. As a result, the bead is retained in the bead-retaining space. Meanwhile, the flow of the reagent causes the bead 502 to move again into a channel portion.

Figure 6:
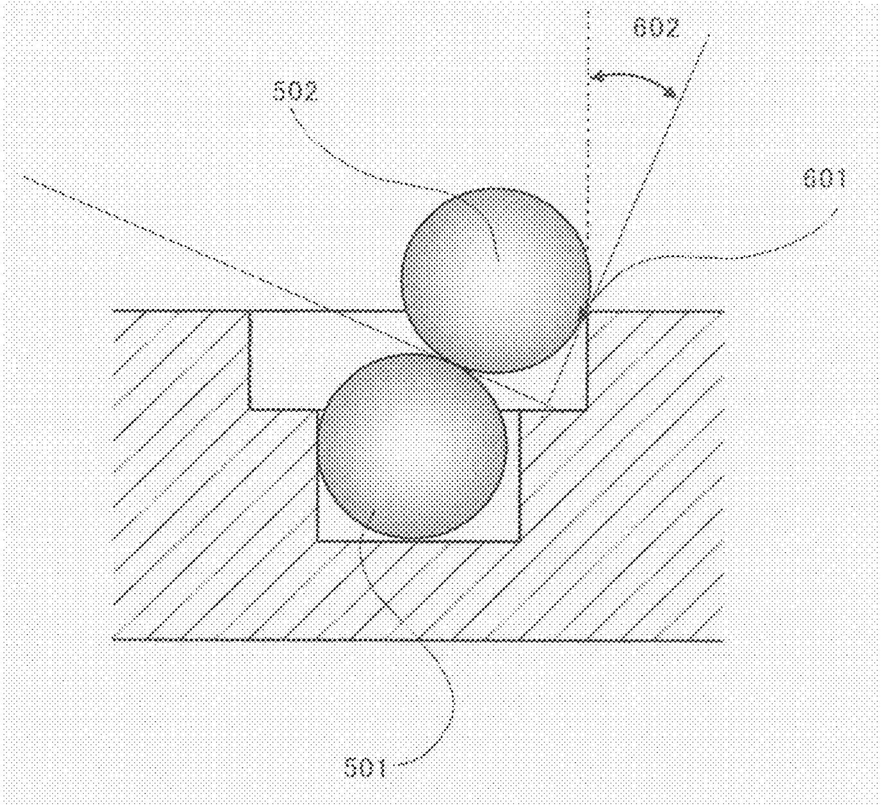
FIG. 6 shows an explanatory view of the retention of a bead and the exiting of a bead.

FIG. 6 shows the retention of a bead and the exiting of a bead. In a condition in which beads 501 and 502 are in contact with each other, the bead 502 is in contact with the wall surface of a cell at a tangent point 601. The angle formed between the tangent line of the bead and the face (extending from the wall surface in contact with the bead) is denoted by a reference numeral 602. When the angle is not zero, the flow of the reagent causes the bead to exit. Thus, as shown in FIG. 6, in a condition in which a bead-retaining space contains a single bead, if an angle formed as a result of the contact between the $2^{nd}$ bead 502 and the cell is larger than zero, at which the tangent line of the bead is parallel to the cell wall surface, the $2^{nd}$ bead 502 is allowed to exit. Therefore, a condition in which a single minute reaction cell retains a single bead alone is satisfied.

Figure 7:
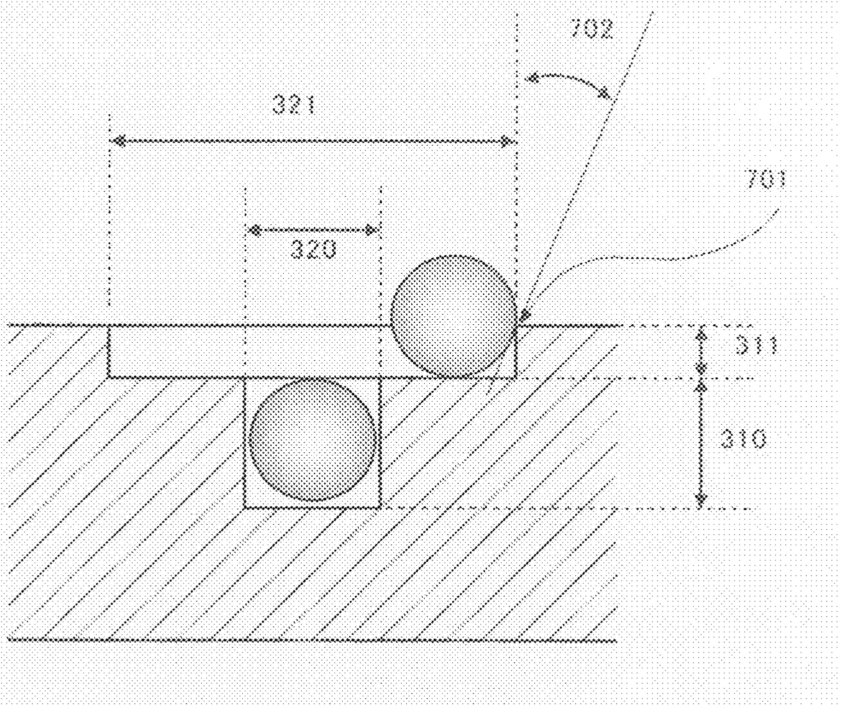
FIG. 7 shows an explanatory view of the retention of a bead and the exiting of a bead in a case in which the diameter of a reagent reaction space is large such that a $1^{st}$ bead and a $2^{nd}$ bead in a bead-retaining space are not in contact with each other.

FIG. 7 shows an example in which the diameter 321 of a reagent reaction space is large enough such that a $1^{st}$ bead in a bead-retaining space is not in contact with a $2^{nd}$ bead. Also in this case, if an angle 702 is larger than zero with respect to a tangent point 701, it is expected that a single minute reaction cell retain a single bead alone. In order to obtain an angle 702 that is larger than zero, it is necessary for a height 311 to satisfy the condition of height 311<"r/2."

Figure 8:
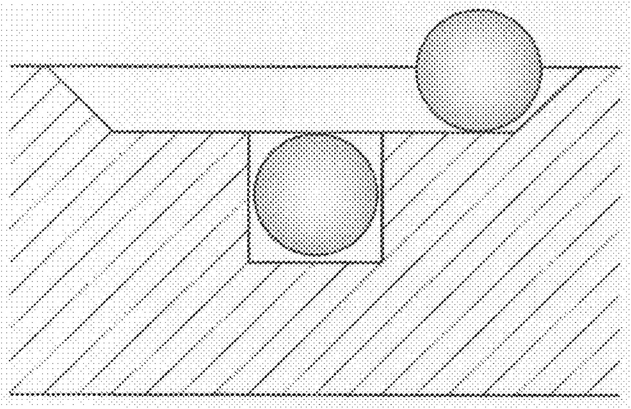
FIG. 8 shows an explanatory view of the retention of a bead and the exiting of a bead in a case in which a reagent reaction space has an inclined wall surface.

FIG. 8 shows an example in which a reagent reaction space has an inclined wall surface. As shown in the figure, when a reagent reaction space has an outward inclined wall surface such that the wall surface is not oriented vertically with respect to the flow of the reagent, it is possible to cause the $2^{nd}$ bead to exit with greater ease.

As described above, the device of the present invention is constructed in a manner such that a single bead is retained in a single minute reaction cell (1 bead/1 minute reaction cell). By repeatedly shaking a reagent from side to side, the number of reaction cells retaining no beads can be easily reduced.

Formation of Separate Reagent Reaction Spaces and Nucleic Acid Amplification

When the above condition (1 bead/1 minute reaction cell) is achieved, all excessive beads are discharged from the flow cell. Thereafter, a target molecule, a primer necessary for nucleic acid amplification, and a reagent such as an enzyme are introduced into the flow cell such that minute reaction cells are filled therewith. In this case, the volume of a reagent in a single cell is obtained by subtracting the volume of a single bead from the volume of a minute reaction cell. Thus, the target molecule concentration is diluted to a level at which a single cell can contain a single molecule. In addition, the probability that no target molecule would be contained in a cell becomes high at a high degree of dilution. However, this is not problematic in the present invention because the occurrence or nonoccurrence of amplification is verified after the termination of amplification. Instead, it is important to reduce the probability of two molecules being simultaneously contained in a reaction cell.

Figure 9:
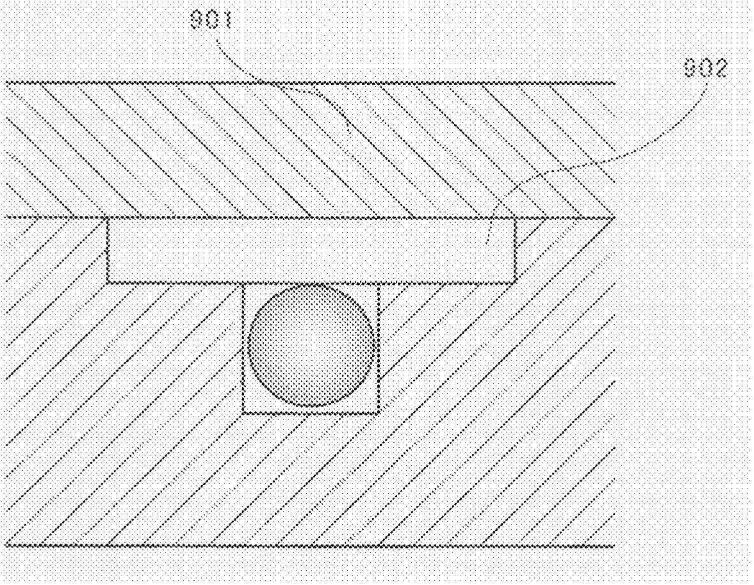
FIG. 9 shows formation of separate minute reaction cells.

FIG. 9 shows formation of separate minute reaction cells (reagent reaction spaces). As shown in FIG. 9, a flow cell is disassembled after introduction of a reagent and then a top plate 901 is placed over the cells. Accordingly, individual minute reaction cells each having a reagent reaction space 902 therein are separately formed. As a result, nucleic acid amplification can be performed in each minute reaction cell containing a single bead in an independent manner.

Figure 10:
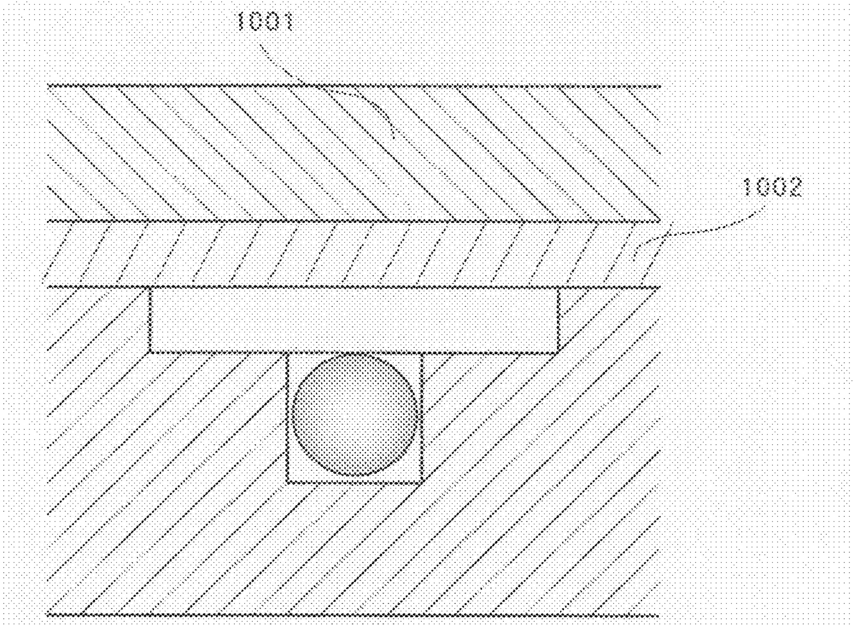
FIG. 10 shows a structure in which a top plate has a two-layer structure.

FIG. 10 shows an example in which a top plate has a two-layer structure. As shown in this figure, when a top plate has a two-layer structure comprising a main body 1001 and an elastic and thin sealing material 1002 such as silicone rubber, formation of separate reagent reaction spaces can be further secured.

Figure 11:
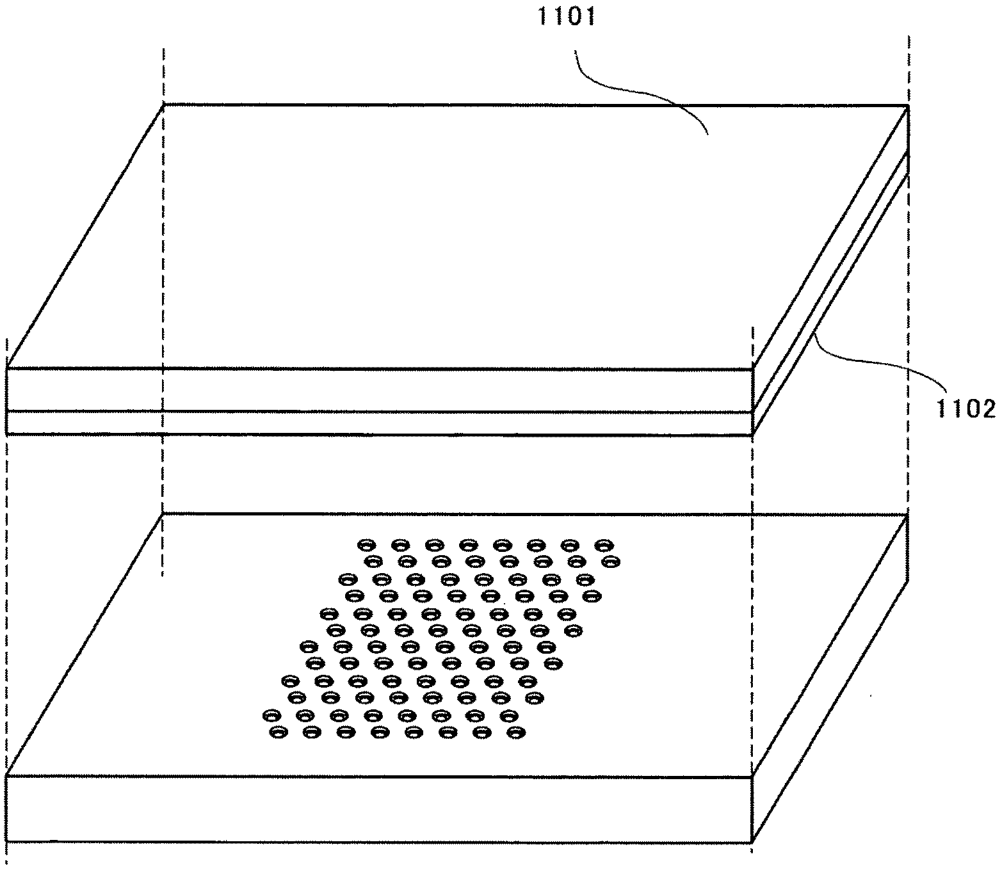
FIG. 11 shows an overall view of a device in which minute reaction cells are separately formed.

FIG. 11 shows an overall view of a device in which reagent reaction spaces are separately formed. As shown in FIG. 11, every minute reaction cell has an independent space when covered with a single top plate (having a two-layer structure comprising a main body 1101 and a sealing material 1102 in this example). In the case of the structure shown in FIG. 11, nucleic acid amplification can readily be performed using a conventional thermal cycler for glass slides, provided that the thickness of the device is 2 mm or less. After nucleic acid amplification, all beads are collected and the occurrence or nonoccurrence of nucleic acid amplification is verified. The occurrence or nonoccurrence of nucleic acid amplification can be verified by a method described in an existing report (PNAS, Vol. 100, No. 15, pp. 8817-8822 (2003)) or by other methods.

EXAMPLE 2

In this example, DNA amplification using beads 50 μm in diameter as solid phases was examined. The results are described herein. Regarding sizes of the minute reaction cells used, diameters 320 and 321 shown in FIG. 3 were 80 μm and 500 μm, and heights 310 and 311 shown in FIG. 3 were 40 μm and 20 μm, respectively. Minute reaction cells were produced via nanoimprinting with the use of polycarbonate as a material. Such minute reaction cells exhibit water repellency when produced; however, they can be hydrophilized via surface treatment. For example, there are well-known methods such as a method involving washing the surfaces of cells with an aqueous solution containing an amphiphilic polymer such as PEG and a method involving irradiation with an ultraviolet lamp for several minutes (Anal. Chem. 2001, 73, 4196-4201). Herein, irradiation with a mercury lamp (40 mW/$cm^2$) for 10 minutes was carried out such that hydrophilization was achieved while coloring was inhibited. The beads used were beads made of zirconia as a material. Zirconia beads have a specific gravity of as large as 5 to 6 and thus they easily precipitate in cells via gravity. Therefore, it was easy to create the aforementioned 1-bead condition. The surface of a bead had a 20-base oligomer connected thereto with a C12 linker. Such an oligomer has a sequence identical to the sequence of one of primers for amplification of a DNA molecule to be amplified and it functions as an amplification primer. In addition, when mRNA is amplified, beads each having a (polyT) oligomer connected to the surface thereof with a C12 linker can be used. In such a case, the technique described in JP Patent Publication (Kokai) No. 2007-319028 may be applied.

In this Example, the total volume of minute reaction cells covered with a top plate is approximately 4,128 pL. The volume of each single bead is approximately 65 pL. Thus, the total volume of a reaction solution in minute reaction cells each containing a single bead is approximately 4,063 pL. When sample DNA to be amplified is adjusted to have a final concentration of approximately 0.4 fmol/L or less, it is possible to allow a single minute reaction cell to contain a single molecule.

Gene amplification was carried out as described below. In addition to sample DNA, a PCR reaction solution with the composition of table 1 was used as a reaction solution to be introduced into minute reaction cells. The F primer has a sequence identical to the sequence immobilized on the bead surface. For the temperature cycle for amplification, a cycle of 94° C. for 15 seconds, 56° C. for 30 seconds, and 70° C. for 30 seconds was repeated 40 times. As a result, an unwound DNA amplified product that was formed continuously following the F primer was obtained on the bead surface.

TABLE 1

Table 1: PCR amplification reagent conditions

| | |
|---|---|
| Tris-HCl (pH 8.8) | 67 mM |
| $NH_4SO_4$ | 16.6 mM |
| $MgCl_2$ | 6.7 mM |
| Mercaptoethanol | 10 mM |
| dNTPs | 1 mM |
| F primer | 0.05 μM |
| R primer | 25 μM |
| Taq polymerase | 15 units |

EXAMPLE 3

In the present invention, minute reaction cells have columnar or conical shapes. When a spherical bead is used, a columnar or conical cell has a horizontal cross section homologous to the central (horizontal) cross section of such bead. In such a case, a reagent reaction space surrounds the bead in an isotropic manner (360 degrees) with respect to the center of the bead, and thus a columnar or conical cell is appropriate for immobilization of amplified products on the bead.

However, in view of the objective of the present invention, the cell shape is not limited to columnar and conical shapes. Moreover, in view of appropriateness in terms of production, a non-columnar or non-conical shape might be better in some cases. For instance, as described above, when a device obtained by nanoimprinting on an organic resin is used, the ease of preparation of a stamper used for producing such device is important in practice. Stampers are widely used in, for example, general semiconductor production processes. Pattern formation is readily performed by light exposure with the use of a mask. However, in such case, if curved shapes are drawn on a mask, the number of processes increases. Therefore, hexagonal cells having approximately circular cross sections were produced herein, and it was confirmed that they functioned as in the above cases.

Figure 21:
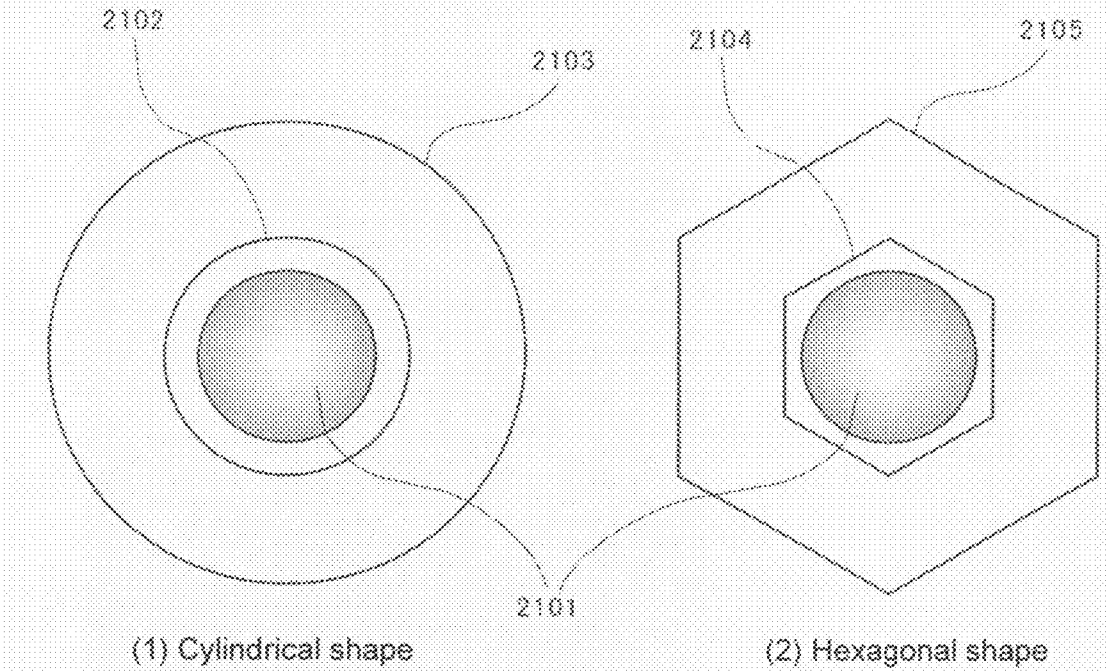
FIG. 21 shows an explanatory view of a case in which a single bead is captured in a minute reaction cell.

FIG. 21 shows explanatory views of cases in each of which a single bead is captured in a minute reaction cell. The graphic (1) is an example of a columnar cell and the graphic (2) is an example of a hexagonal cell. When a bead 2101 is captured, the reference numeral 2102 denotes a capturing space and a reagent reaction space is the region between "2102" and "2103" in the case of the columnar cell. In the case of the a minute reaction cell having a hexagonal columnar shape, the reference numeral 2104 denotes a capturing space and a reagent reaction space is the region between "2104" and "2105." It was confirmed that the hexagonal columnar cell functioned as in the case of the columnar cell.

EXAMPLE 4

Example 4 shows a device in which minute reaction cells each having two different bead-retaining spaces are separately formed (in a one-to-one manner).

Figure 12:
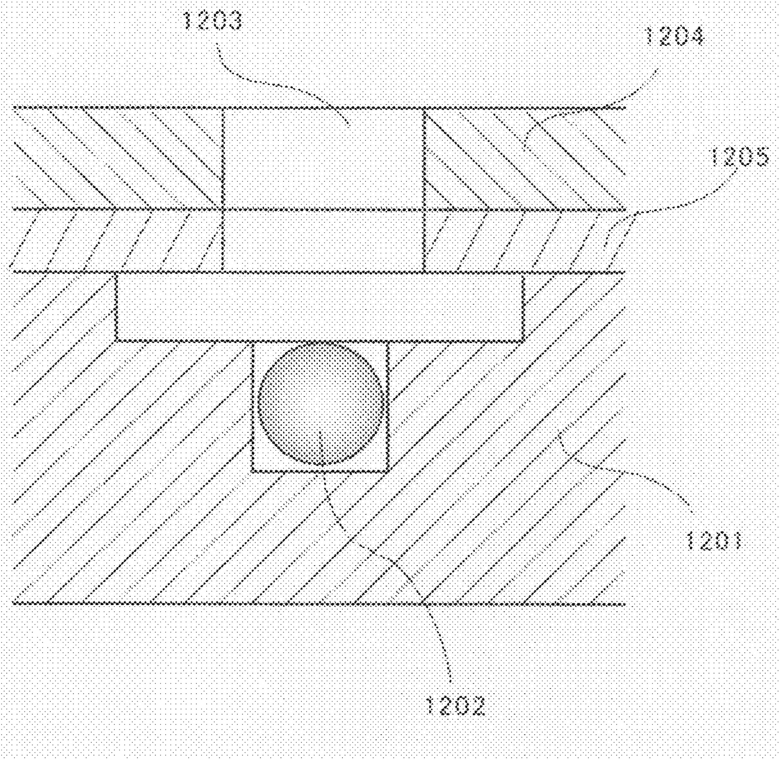
FIG. 12 shows an explanatory view of the retention of a bead and the exiting of a bead in a device in which two types of beads are used.

FIG. 12 shows a condition in which a top plate 1204 having a $2^{nd}$ bead-retaining space 1203 and a sealing material 1205 are placed on a minute reaction cell 1201 retaining a $1^{st}$ bead 1202. Flow cell formation is carried out on the thus obtained device as in the case of the device 401 of Example 1, which is shown in FIG. 4, followed by introduction of a reagent containing $2^{nd}$ beads.

Figure 13:
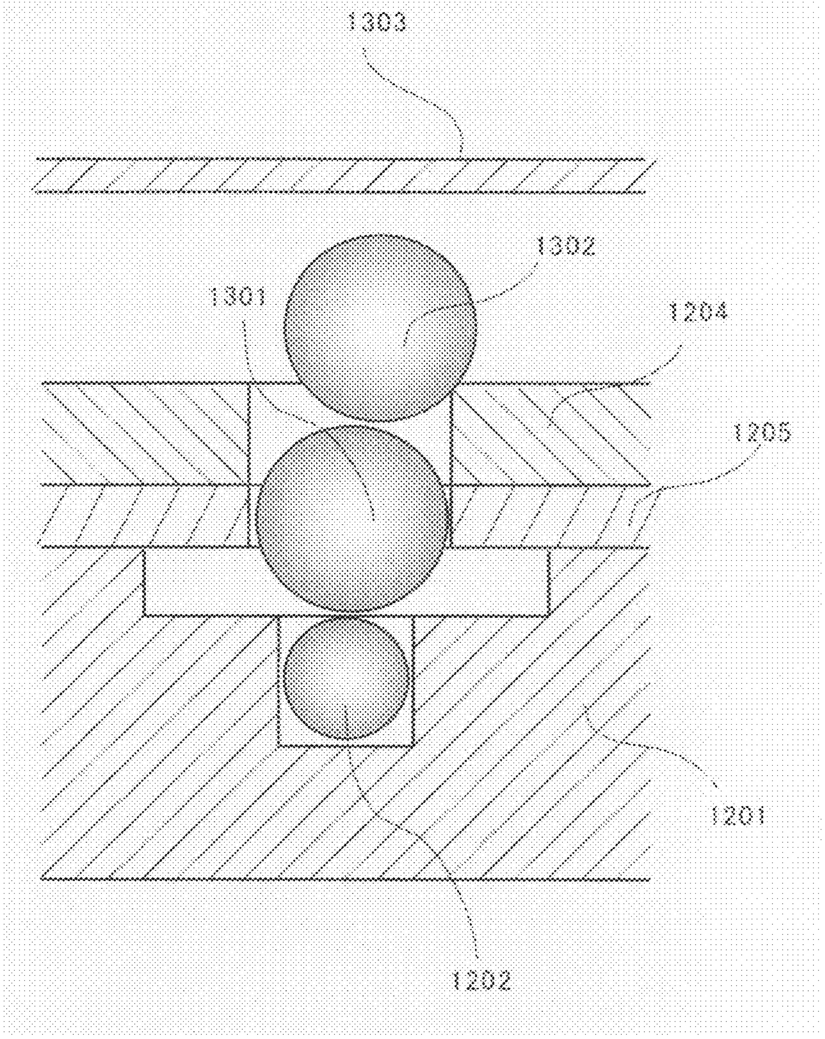
FIG. 13 shows an explanatory view of the retention of a bead and the exiting of a bead in a case in which a $2^{nd}$ bead is larger than a $1^{st}$ bead.

FIG. 13 shows the inflow and the retention of $2^{nd}$ beads 1301 and 1302 in the case of a device on which a flow cell is formed under a top plate 1303. FIG. 13 shows a specific example in which the $2^{nd}$ beads are larger than the $1^{st}$ bead 1202. In such a case, as in the case of Example 1, among the $2^{nd}$ beads, the bead 1301 is retained in the bead-retaining space 1203, but the bead 1302 is not retained therein and exits therefrom again. As a result, the minute reaction cell retains a single $1^{st}$ bead 1202 and a single $2^{nd}$ bead 1301.

Figure 14:
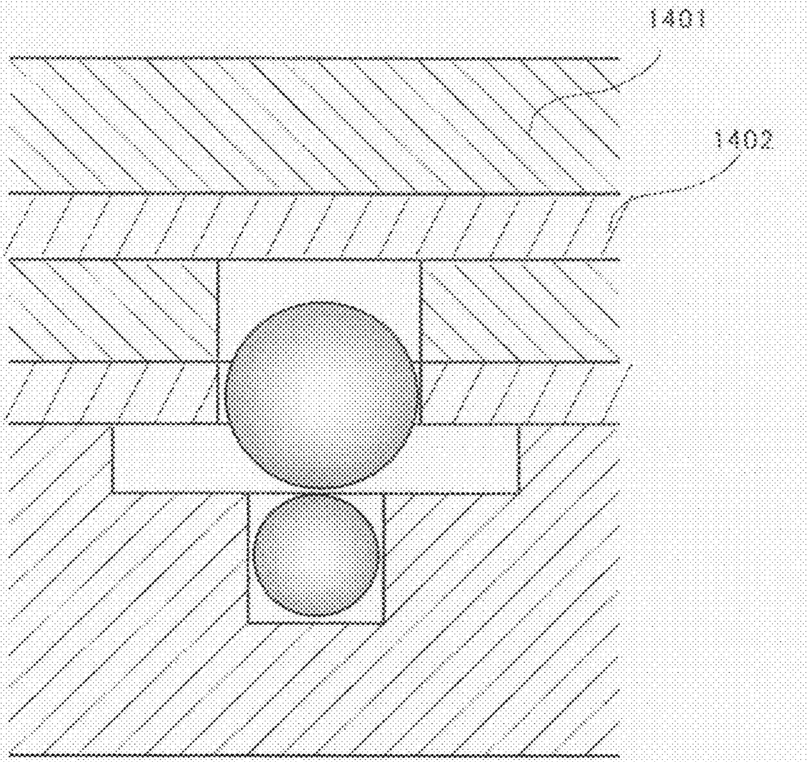
FIG. 14 shows minute reaction cells that are separately formed in a manner such that two different beads are separately contained therein.

FIG. 14 shows a minute reaction cell that is separately formed when covered with a top plate. As shown in FIG. 14, after the operation described above, a top plate 1401 and a sealing material 1402 are installed such that formation of separate minute reaction cells can be realized. In such a structure, a sample can be immobilized on the surface of one bead before amplification and an amplified product can be immobilized on the surface of the other bead.

Figure 15:
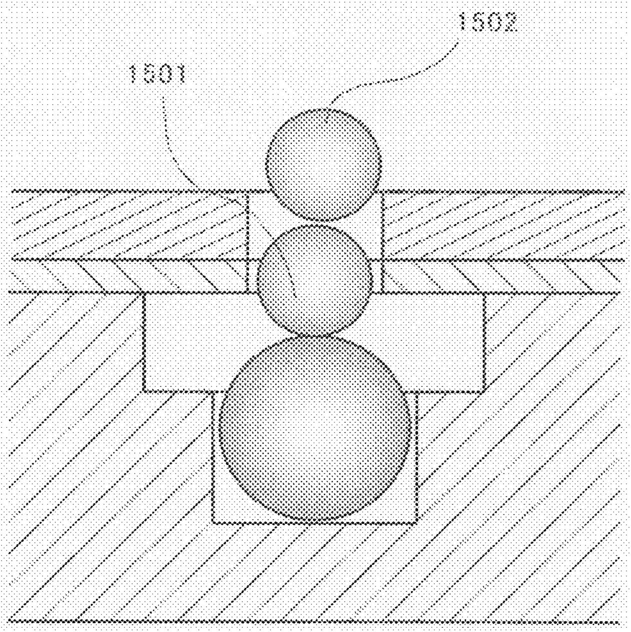
FIG. 15 shows an explanatory view of the retention of a bead and the exiting of a bead in a case in which a $2^{nd}$ bead is smaller than a $1^{st}$ bead.

FIG. 15 shows an example in which $2^{nd}$ beads are smaller than a $1^{st}$ bead. Also in this case, formation of separate minute reaction cells can be realized with the operation described above.

EXAMPLE 5

Example 5 shows a device having a structure in which a bead-retaining space and a reagent reaction space are connected to each other with a capillary.

Figure 16:
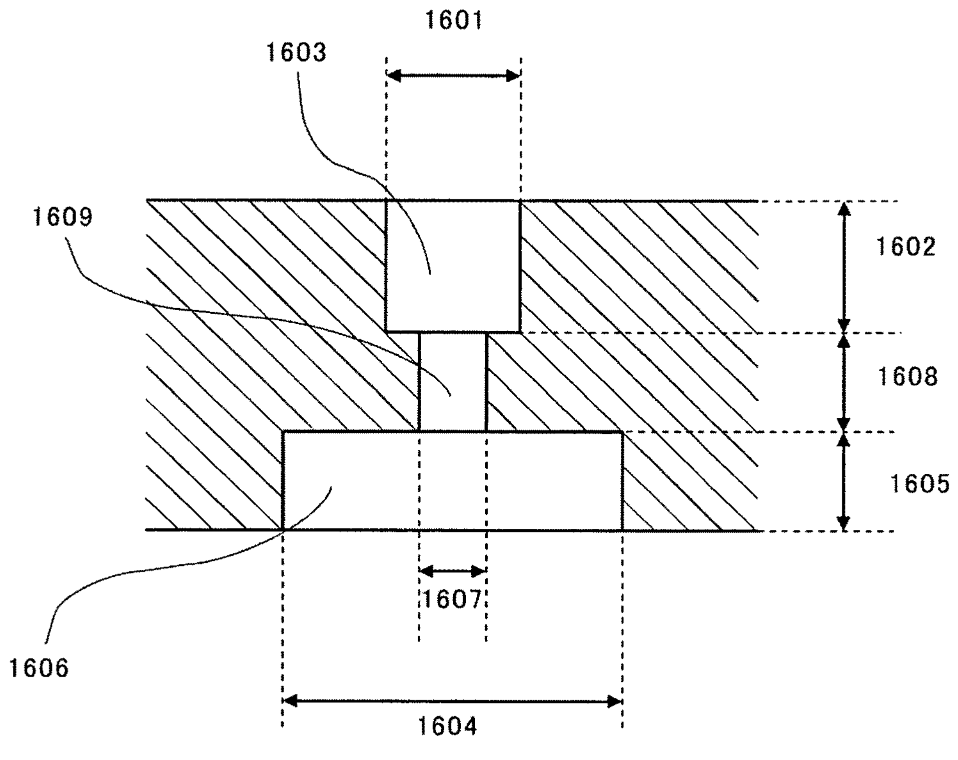
FIG. 16 shows an explanatory view of a minute reaction cell having a structure in which two spaces are connected to each other with a capillary.

FIG. 16 shows a structure in which two spaces are connected to each other with a capillary. In this case, a $1^{st}$ space 1603 with a diameter 1601 and a height 1602 and a $2^{nd}$ space 1606 with a diameter 1604 and a height 1605 are connected to each other with a capillary 1609 with a diameter 1607 and a height 1608. In the case of such device, the 1st space is used as a bead-retaining space and the 2nd space is used as a reagent reaction space.

Figure 17:
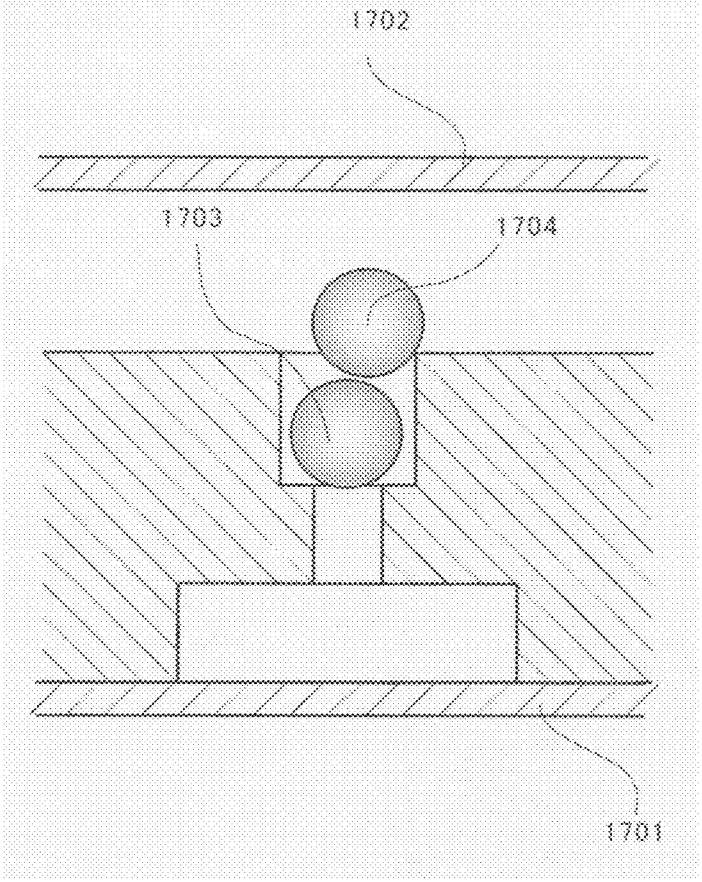
FIG. 17 shows flow cell formation in the device.

FIG. 17 shows flow cell formation in the case of the above device. As shown in FIG. 17, flow cell formation is carried out with the use of a top plate 1702 as in the case of FIG. 4 and an aqueous solution containing beads is introduced while the 2nd space is closed with a bottom plate 1701, resulting in retention of a bead 1703. As in the case of the above example, a bead 1704 exits again and thus a condition in which a minute reaction cell retains a single bead is achieved.

Figure 18:
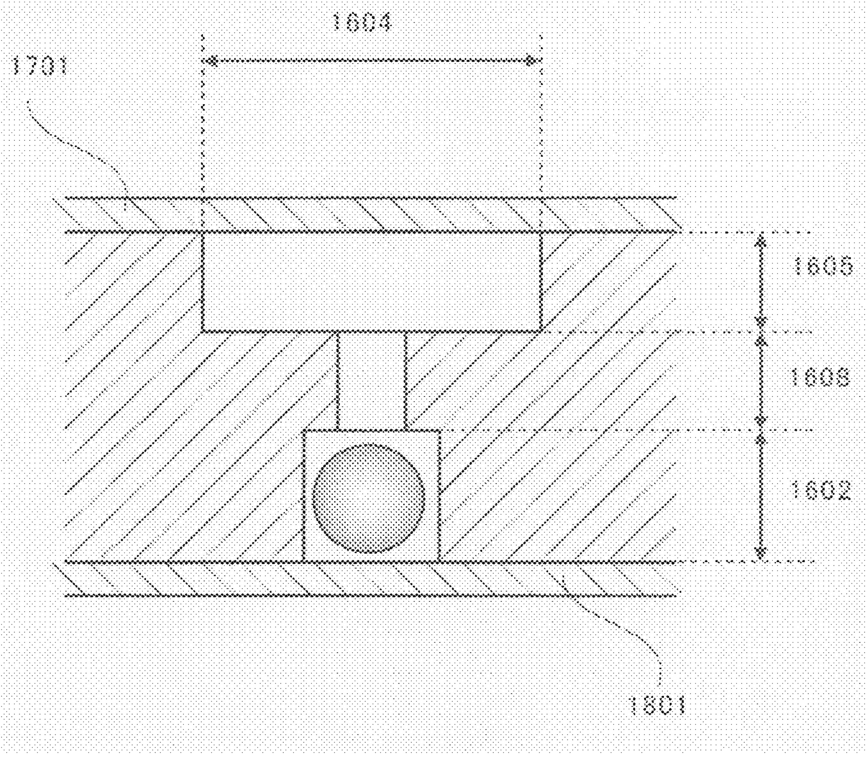
FIG. 18 shows formation of separate minute reaction cells.

FIG. 18 shows formation of separate minute reaction cells (reagent reaction spaces). As shown in FIG. 18, when a flow cell is disassembled, a 1st space is closed with a plate, and the space is turned upside down, a device having a bead-retaining space closed with a bottom plate 1801 is realized as shown in FIG. 18. Under such conditions, a plate 1701 is removed and thus flow cell formation is achieved as shown in FIG. 4 such that a reagent can be introduced into a reagent reaction space. In addition, when the plate 1701 is installed again as shown in FIG. 18, formation of separate minute reaction cells (reagent reaction spaces) can be achieved.

EXAMPLE 6

Example 6 shows a device having a structure in which a 1st bead-retaining space and a 2nd bead-retaining space are connected to each other with a capillary.

Figure 19:
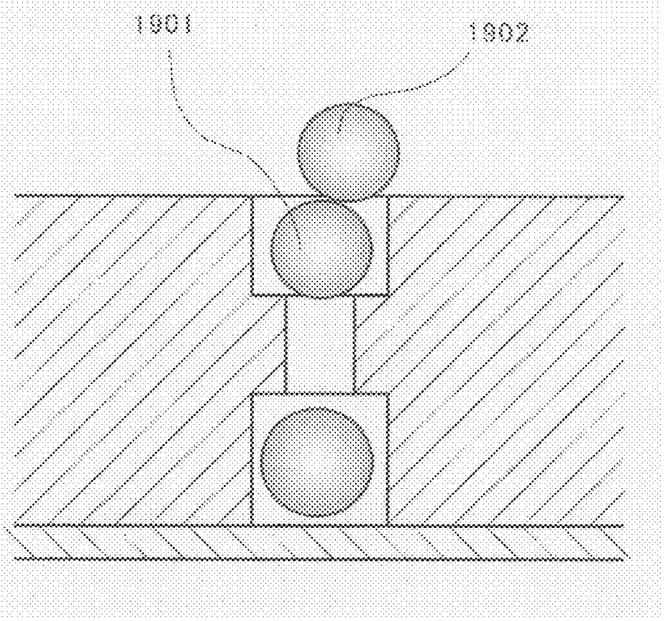
FIG. 19 shows a structure in which a $1^{st}$ bead-retaining space and a $2^{nd}$ bead-retaining space are connected to each other with a capillary.

FIG. 19 shows a structure in which a 1st bead-retaining space and a 2nd bead-retaining space are connected to each other with a capillary. 2nd beads 1901 and 1902 are allowed to flow into a device in which a flow cell is formed as in the case of Example 1 and the bead 1902 is allowed to exit therefrom, such that a minute reaction cell retains a single 1st bead and a single 2nd bead 1901.

Figure 20:
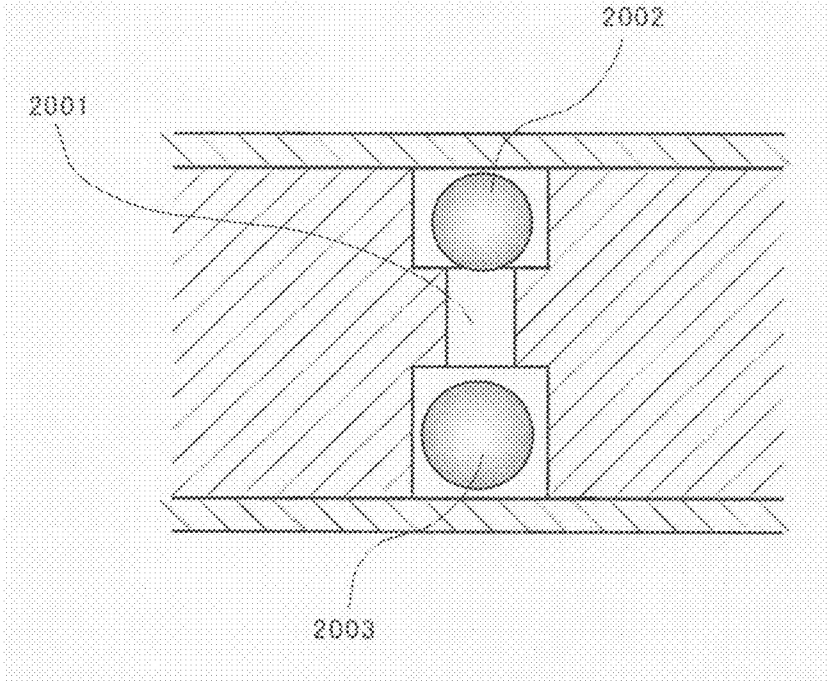
FIG. 20 shows an explanatory view of the retention of a bead and the exiting of a bead in a structure in which a $1^{st}$ bead-retaining space and a $2^{nd}$ bead-retaining space are connected to each other with a capillary.

FIG. 20 shows formation of separate reagent reaction spaces. As shown in FIG. 20, a flow cell is disassembled after introduction of a reagent and a top plate is placed on cells, such that formation of separate minute reaction cells each containing two different beads is achieved. In such case, a reagent reaction space corresponds to a columnar space denoted by a reference numeral 2001 and it also functions as a connecting portion between two bead-retaining spaces.

Preferred embodiments of the use of this example are as follows. In many cases, properties of beads, which are required for DNA amplification on bead surfaces, differ from those required for a variety of processes such as detection, verification, sequencing, and the like with the use of amplified products existing on the bead surfaces. For instance, in the case of DNA amplification on bead surfaces, it is required that the components of an amplification reaction reagent such as a primer and an enzyme be unlikely to adsorb to bead surfaces. In such case, beads made of a material that is a hydrophilic polymer such as sepharose or agarose are often used. Meanwhile, in the cases of a variety of processes such as detection, verification, sequencing, and the like with the use of amplified products existing on the bead surfaces, beads having large specific gravities are easily used in order to prevent the exiting of beads when such beads are used in a flow cell. For such reason, silica beads, zirconia beads, a variety of plastic beads, metal beads, and the like are used. In this Example, an amplified product is first obtained as a result of amplification on the surface of a sepharose amplification bead 2002 with the steps described in the above Examples. Then, a zirconia bead having large specific gravity is used as a detection bead 2003. A reagent reaction space is filled with a reagent with which PCR amplification can be performed with the use of DNA on the surface of a bead 2002 as a template. Under such conditions, the device was attached to a thermal cycler and PCR amplification was carried out in minute reaction cells, such that an amplified product of DNA to be detected was obtained as a result of amplification on the surface of each detection bead 2003.

INDUSTRIAL APPLICABILITY

The present invention can be applied in various fields of life science, medicine, food, and the like, in which gene analysis techniques are required.

What is claimed is:

1. A nucleic acid amplification device comprising:

a plurality of reaction cells each comprising a set of a first space, a second space, and a capillary connecting the first space and the second space, at least one of the first space and the second space capable of retaining a single bead; and a removable cover completely covering the first space or the second space, and thereby isolating the first space, the second space and the capillary of each respective reaction cell of the plurality of reaction cells from the first space, the second space and the capillary of the remaining plurality of reaction cells of the nucleic acid amplification device, wherein the first space and the second space have respective diameters which are larger than a diameter of the capillary, and wherein the first space, the second space and the capillary are stacked vertically on top of each other in a direction perpendicular to the respective diameters' dimension direction.

2. The nucleic acid amplification device of claim 1, wherein both the first space and the second space are each capable of retaining a single bead.

* * * * *